United States Patent [19]

Wu et al.

[11] 4,224,942
[45] Sep. 30, 1980

[54] CELL FRACTIONATING METHOD

[75] Inventors: Anna F. Wu; Tai T. Wu, both of Chicago, Ill.

[73] Assignee: Northwestern University, Evanston, Ill.

[21] Appl. No.: 33,118

[22] Filed: Apr. 25, 1979

[51] Int. Cl.³ .............................................. B03D 3/00
[52] U.S. Cl. ................................... 128/214 R; 209/5; 209/208; 210/927
[58] Field of Search .................... 210/42, 54, 59, 45, 210/83, 84, DIG. 23; 209/5, 172, 173, 208; 128/272, 1 R, 214 D, 214 R; 424/101

[56] References Cited

U.S. PATENT DOCUMENTS

| | | | |
|---|---|---|---|
| 3,677,710 | 7/1972 | Hirsch | 210/83 |
| 3,709,791 | 4/1973 | Lichtenstein | 210/DIG. 23 |
| 3,858,795 | 1/1975 | Joyce | 210/DIG. 23 |
| 4,130,642 | 12/1978 | Kikugawa | 424/101 |

FOREIGN PATENT DOCUMENTS

| | | | |
|---|---|---|---|
| 562283 | 9/1977 | U.S.S.R. | 424/101 |
| 578085 | 9/1977 | U.S.S.R. | 210/DIG. 23 |

OTHER PUBLICATIONS

A. F. Wu and T. T. Wu, Velocity Sedimentation in Isotonic Saline and Sucrose Buffer as a Possible Method of Fractioning Normal Erythrocytes, Preparative Biochemistry, 8:347–361, (1978).
R. C. Lief and J. Vinograd, The Distribution of Buoyant Density of Human Erythrocytes in Bovine Albumin Solutions, Proc. Nat. Acad. Sci., 51:520–524, (1964).
N. Catsimpoolas, Methods of Cell Separation (Chapter on Preparative Density Gradient Electrophoresis and Velocity Sedimentation at Unit Gravity of Mammalian Cells, vol. 1, pp. 1–24, Plenum Press, N.Y., 1977.
Williams, W. J., E. Beuthler, A. J. Erslev, and R. W. Rundles, Hematology, pp. 1375–1377, McGraw-Hill, N.Y., 1972.

Primary Examiner—Ernest G. Therkorn
Attorney, Agent, or Firm—Tilton, Fallon, Lungmus & Chestnut

[57] ABSTRACT

A method for fractionating red blood cells by velocity sedimentation to remove those cells approaching lysis while at the same time maintaining the transfusability of the remaining cells.

12 Claims, 3 Drawing Figures

CELL FRACTIONATING METHOD

BACKGROUND AND SUMMARY

It is well known that a sample of normal human erythrocytes does not consist of a homogenous population. The age of such cells varies from zero to 120 days, and their densities range between 1.065 to 1.095 grams (g) per milliliter (ml) with the reticulocytes and youngest erythrocytes having the lowest density. See A. F. Wu and T. T. Wu, Velocity Sedimentation in Isotonic Saline and Sucrose Buffer as a Possible Method of Fractionating Normal Erythrocytes, Preparative Biochemistry, 8:347–361 (1978), and references cited therein.

As described in the aforementioned publication, when red cells mature their density gradually increases. Most of them acquire a biconcave disc shaped form known as discocytes, while some of them display short spicules projecting from a central spheroid and are designated echinocytes. Their dimensions are also quite varied. In hypotonic solutions, erythrocytes tend to burst but not all at once. Roughly half of them will lyse in 0.40 to 0.45% saline. On storing such cells for one day, the concentration of saline required to maintain half lysis must be increased to 0.47 to 0.58%. The longer red cells are stored, the more fragile they become. Such osmotic fragility does not appear related, however, to the reticulocyte count of the blood nor to the age of the erythrocytes.

It has been customary to assume that the age of erythrocytes varies linearly with density and, therefore, prior efforts to investigate the different cell populations of erythrocyte samples have commonly utilized equilibrium sedimentation techniques. R. C. Leif and J. Vinograd, The Distribution of Buoyant Density of Human Erythrocytes in Bovine Albumin Solutions, Proc. Nat. Acad. Sci., 51:520–524 (1964). In a linear density gradient, human red cells exhibit only one peak centered around 1.08 g/ml, but in a stepwise gradient consisting of isotonic solutions with densities of 1.07, 1.08, and 1.09 g/ml and a cushion at the bottom, four bands of cell populations based on differences in buoyant density have been identified.

Velocity sedimentation in a density gradient of bovine serum albumin has also been used experimentally to investigate human red cell populations but again only one peak was obtained. N. Catsimpoolas, Methods of Cell Separation, Vol. 1 (Plenum Press, N.Y., 1977). Whether by velocity sedimentation or equilibrium sedimentation, such fractionation of red cells has been carried out only on an experimental basis for the purpose of investigating red cell populations. Indeed, the density gradient medium used in such experimental work (bovine serum albumin) has the effect of coating the cells and precludes their subsequent use in clinical procedures.

One aspect of this invention lies in the recognition that for many of those patients suffering from various hemolytic anemias and other diseases requiring transfusions of packed red cells, the presence of damaged or drying cells in the transfusate only increases the burden on the patient's system and is especially undesirable where, for example, the patient's condition is complicated by congestive heart disease, renal failure, cirrhosis, or the like. This invention is thus concerned with a simple but highly effective procedure for fractionating a heterogenous red cell population, such as that of donor blood which has been stored for a number of days awaiting transfusion, to exclude those cells which are approaching lysis and are therefore nearing the end of their useful life.

Another aspect of this invention resides in the discovery that although red cells are known to increase in density as they become older, buoyant density fractionating procedures are unsuitable for this purpose because such procedures would result in the elimination of older cells but not necessarily those nearing lysis, and that on the other hand, a velocity sedimentation procedure may be used effectively to exclude those cells approaching lysis regardless of their age. The result is a method which may be used effectively to segregate cells according to their viability, and which allows the retention for transfusion of those human red cells that are more viable regardless of their age or density.

In brief, the method of this invention lies in exposing an entire red cell population to velocity sedimentation in a solution of isotonic saline buffered to a pH of about 7.4 and containing a soluble cell-compatible density-adjusting agent in an amount sufficient to adjust the solution to a density within the range of about 1.005 to 1.015. Particularly effective results have been achieved when the density-adjusting agent is a disaccharide such as sucrose. The red cells are collected and separated into at least two fractions based on differences in sedimentation rates, and that fraction containing the slower sedimenting cells, particularly echinocytes, is excluded. The normal red cells of the retained fraction may then be washed in isotonic saline (to remove the sucrose) and then transfused.

Other features, advantages, and objects of the invention will become apparent as the specification proceeds.

DRAWINGS

DETAILED DESCRIPTION

Figure 1:
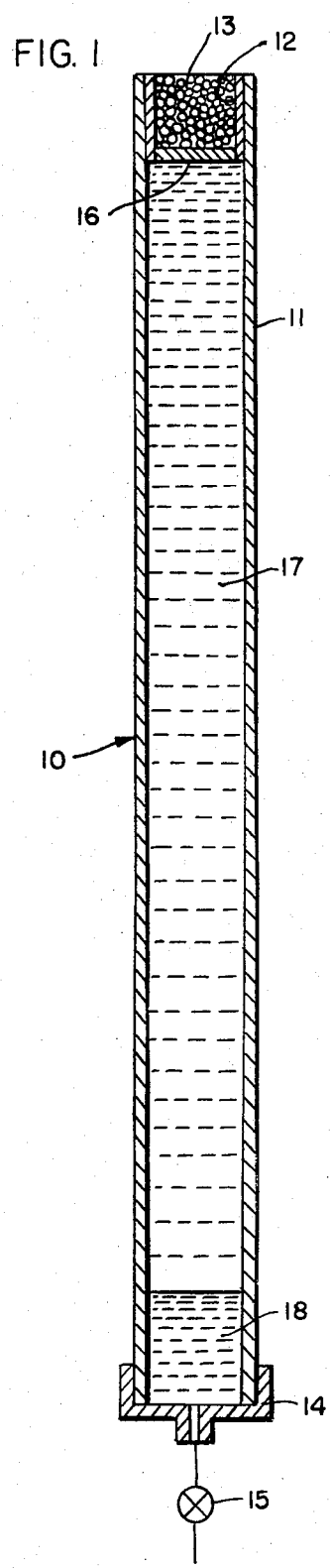
FIG. 1 is a somewhat schematic vertical sectional view of a velocity sedimentation column used in the method of this invention.

Referring to FIG. 1, the numeral 10 designates a velocity sedimentation column comprising a tube 11, a sample applicator 12 for supporting a heterogenous suspension of red cells 13, and an end fitting 14 at the lower end of the column for drawing off fractions as required, the fitting being associated with valve 15. The lower end of receptacle 12 is provided with a porous bottom wall 16 through which the red cells may readily pass to enter the fluid contained within the main portion of the column.

Within the column directly below the receptacle or sample applicator 12 is a primary fluid layer 17 composed of a solution of isotonic saline buffered to a pH of about 7.4 and containing a suitable density-adjusting agent in an amount sufficient to increase the density of the solution to a level substantially above the density of the liquid (isotonic saline) in receptacle 12 but less than the density of red cells (approximately 1.08). For a gravity column, in contrast to one that might utilize centrifugal force, layer 17 should have a density within the general range of 1.005 to 1.015 g/ml, the preferred density being about 1.010 g/ml.

The density-adjusting agent must not only be water soluble but it must also be non-reactive with respect to red cells. For example, although bovine serum albumin has been used as a density-adjusting agent in prior work by others involving equilibrium and velocity sedimentation (see references previously cited), such an agent is not acceptable here because it would coat the red cells with a foreign protein and render them unsuitable for subsequent transfusion. On the other hand, disaccharides such as sucrose and polysaccharides such as dextran may effectively augment the density of the solution without appreciably affecting the transfusability of the cells. Sucrose is preferred over glucose because the former does not tend to penetrate the cell membranes, may be removed from the cells following fractionation, and is in any event readily metabolized should trace amounts remain on the cells during subsequent transfusion.

The density of upper layer 17 may be varied to fall within the range of about 1.005 to 1.015 g/ml by simply adjusting the relative proportions of the isotonic saline and the density-adjusting agent of that layer. Where sucrose is used as the density-adjusting agent, a saline-sucrose volume ratio within the range of 6:1 to 8:1 (preferably 7:1) may be used.

The lower layer 18 is of greater density than layer 17 to serve as a cushion for the descending cells and to facilitate removal of the cell fractions from the bottom of the column. The isotonic lower layer may be of essentially the same composition as upper layer 17 except for a reduction or elimination of the saline component. Thus, the lower layer may take the form of an isotonic sucrose solution buffered to a pH of about 7.4. While the provision of a lower layer 18 is believed desirable for the reasons given and is particularly useful in experimental procedures, it is believed that such layer may be omitted entirely and that the entire column may be filled with the solution described in connection with upper layer 17.

Any suitable physiological buffer may be used to maintain the pH of the upper and lower layers at about 7.4. A sodium phosphate buffer (0.01 M) is especially effective but other buffers, such as a glycine buffer, may be used.

In carrying out the method, a quantity of packed erythrocytes are first washed in normal saline and are then resuspended in 2-4 times their volume of isotonic saline buffered to a pH of about 7.4. Such suspension is then introduced into the receptacle or applicator 12 of the column. The column is maintained under refrigeration (approximately 4° C.) for a sufficient interval to produce distribution of the cells within upper layer 17. It is believed apparent that the length of that interval depends on the size of the column and the density of solution 17. When the red cells become distributed throughout layer 17, the contents of the column are removed in at least two fractions, the second fraction containing the slower sedimenting cells of the total red cell population. The cells of the first fraction are retained for transfusion or other use, whereas the cells of the second fraction, consisting primarily of echinocytes, are discarded. Where transfusion is intended, the retained fraction is centrifuged and the cells are washed in buffered isotonic saline to free them of sucrose (or other density-adjusting agent) that may have coated the cells during the fractionation procedure.

The volume of the final (discarded) fraction will of course depend primarily on the length of time the blood has been stored. Freshly drawn blood has a relatively small proportion of echinocytes and may require no fractionation at all, whereas blood that has been stored 15-21 days may have such a substantial proportion of its red cells in the echinocyte phase that separation of the final fraction would reduce the total red cell volume by 20% or more. Thus, the final fraction, although a minor fraction relative to the initial fraction(s) containing the retained cells, would vary considerably in accordance with the age of the blood and the operation of the fractionating column.

It is important to note that the fractionating of red blood cells in accordance with this method does not depend primarily on the density of the cells traveling through the column. If that were the case, then the initial fraction(s) would be expected to contain the older, heavier cells, while the final fraction would contain the younger and presumably more viable cells. Instead, the general observation is that the younger and more viable red cells traverse the column more quickly because, for reasons which are not fully known, such cells tend to aggregate in small clumps or clusters of 5 to 10 cells, quite different from rouleau formation under the influence of plasma proteins. Because of such cluster formations, the healthy cells (discocytes) have effective radii substantially larger than unclustered cells and, in accordance with the following equation describing downward cell velocity in a density gradient, travel more quickly through the medium than single cells:

$$V_x = (2r^2 g/9 n_x)(p_c - p_x)$$

where $V_x$ is the instantaneous velocity of cells at any position x in the column (cm/sec); r is the cell radius (cm); g is the acceleration of gravity (980.7 cm/sec$^2$); $n_x$ is the viscosity of the medium at position x (poises); $p_c$ is cell density (g/cm$^3$); and $p_x$ is the density of the medium at position x (g/cm$^3$). In the present procedure, cell migration downwardly will depend primarily on the radius of the cell (or cell cluster) and less on the density of the cells. While discocytes are not spherical, a number of them sticking together might be approximated as spherical particles for purposes of the standard analysis for velocity sedimentation.

In contrast to the limited clustering of normal discocytes, it has been found that red cells in their echinocyte phase do not cluster and that fact, coupled with the viscous drag that may develop because of the spicule formation, causes such cells to travel more slowly downwardly through the density gradient. As a result, the final fraction(s) may be composed almost entirely of echinocytes. To the extent that red cells in their echinocyte phase (whether such cells are relatively young or relatively old) are believed to be approaching lysis, the fractionating method disclosed herein is useful in separating out the less viable cells of a total red cell population so that the remaining cells may be transfused or used for other purposes.

As brought out in the following examples, this explanation tends to be an oversimplification because the migrating cells actually arrange themselves in multiple peaks which appear representative of different cell populations or sub-populations. Nevertheless, it remains an observable fact that the slowest migrating red cells are those in an echinocyte phase, and such cells, regardless of their age or density, may be readily separated from the remaining cells in their discocyte phase.

EXAMPLE 1

Normal human erythrocytes were obtained from two different sources. The first source, a blood bank, provided packed red cells which had been machine washed once in normal saline. Those cells showed some hemolysis probably due to storage and handling. The second source was a clincial laboratory which supplied samples of whole blood about 5 to 10 hours old and showing no detectable amount of hemolysis. Erythrocytes from the samples of the second source were collected by centrifugation.

Velocity sedimentation was carried out in a K16/40 column (inside diameter 1.6 cm, length 40 cm) from Pharmacia Fine Chemicals, Sweden. Each column was filled with 10 ml of isotonic sucrose solution containing 0.01 M sodium phosphate buffer at pH 7.4 (in the lower part) and with 60 ml of isotonic saline-sucrose (7:1) buffer (in the upper part). A sample applicator or receptacle was fixed at the top of the column just below the meniscus as shown in FIG. 1. Packed erythrocytes were washed once in normal saline and resuspended in three times the volume of isotonic saline buffer. One ml of this suspension was then applied to the top of the column through the sample applicator. After standing at 4° C. for 20 hours, fractions of 1 ml each were collected, giving about 70 fractions. For stored blood cells, some hemolysis might be expected to occur during the run; thus, cells from each tube were centrifuged down and resuspended in 1 ml of isotonic saline buffer for subsequent studies.

Figure 2:
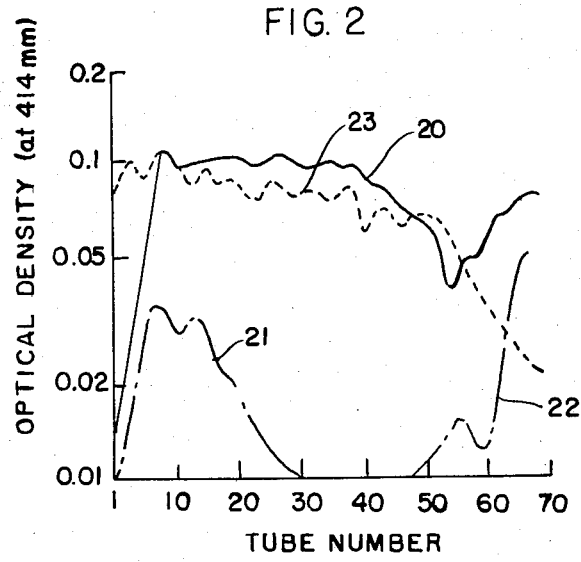
FIG. 2 is a graph revealing the optical density characteristics of different samples of blood fractionated in accordance with this method.

A typical velocity sedimentation run for packed red blood cells from the blood bank is represented by the solid curve 20 in FIG. 2. As compared with the result of buoyant density (equilibrium sedimentation) separation on a linear gradient where only a single peak is normally presented, FIG. 2 reveals a number of distinct peaks.

To determine that such peaks are reproducible from sample to sample, and that the peak locations appear characteristic of particular cell populations or subpopulations, the erythrocytes in tubes 1 through 15 were pooled and collected by centrifugation. They were then applied to an identical second column. Line 21 shows that the peak locations for cells in these 15 tubes were essentially the same as the peak locations in the first run. Similarly, cells from tubes 56 through 70 were pooled, collected by centrifugation, and applied to a further column, and the peaks so developed are represented by line 22 in FIG. 2. Such results strongly suggest that each peak contains cell populations distinct from the rest of the erythrocyte sample.

To determine whether the peaks represented by line 20 are due at least in part to storage and handling of the blood cells, the relatively fresh erythrocytes from the clinical laboratory (second source) were analyzed by the same velocity sedimentation method. The results of a typical run are shown by the dashed curve 23 in FIG. 2. A very fast sedimenting peak is located around tube 5. The deep valley around tube 55 for the blood bank erythrocytes is not found in the curve for the relatively fresh clinical laboratory erythrocytes. Indeed, it will be noted that the two slowest sedimenting peaks for curve 20 around tubes 58 and 70 are completely absent from curve 23. On the other hand, the other peaks between tubes 10 and 50 are essentially reproduced for both samples. It is believed remarkable that for both samples there are 8 peaks located around tubes 10, 16, 21, 27, 34, 38, 44, and 50.

EXAMPLE 2

Microscopic examination of the cells in tube 10 for the samples represented by lines 20 and 23 in FIG. 2 showed that such cells appear as normal discocytes with a tendency to stick together forming clusters of 8 to 10 cells, but not as rouleau. On the other hand, microscopic examination of the cells in tube 50 for both samples reveal that such cells were still discocytes but were evenly distributed on the slides. As to the peaks around tubes 58 and 70 in the line 20 representing red cells from the blood bank, microscopic examination revealed that tube 70 contained only echinocytes which showed no tendency of clumping together. Since echinocytes were rarely found in normal fresh human blood samples, they might well be the result of handling and storage in the blood bank.

EXAMPLE 3

Figure 3:
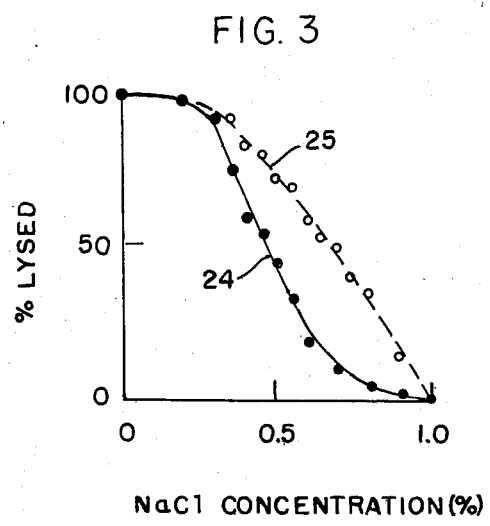
FIG. 3 is a graph showing certain osmotic fragility characteristics of different cell fractions.

Fragility tests were performed for the cells in tubes 10 and 70 of the fractionating sample obtained from the blood bank in an effort to determine whether the drastic difference in shape of such cells might be related to osmotic fragility. The standard osmotic fragility test described by Williams, W. J., E. Beutler, A. J. Erslev, and R. W. Rundles, Hematology, pp. 1375–1377 (McGraw-Hill, N.Y., 1972), was employed except that the range of saline solution used in the study was increased to include 0.0 and 1.0% and that the amount of hemoglobin was estimated by $O.D._{414}$ rather than $O.D._{545}$. As represented by line 24 in FIG. 3, the cells in tube 10 behaved reasonably similar to fresh blood samples in the sense that a typical S-shaped curve was obtained and that the half-lysis point was located around 0.45% saline. On the other hand, cells in tube 70, as represented by line 25, were extremely fragile, requiring 0.68% saline to maintain half-lysis. Furthermore, the shape of the curve was quite atypical. A mixture of these two different types of erythrocytes with various proportions could thus give many types of fragility curves. It is believed that this result may help to clarify the increase of fragility of stored blood, since some portion was on the way to lysis as represented by the echinocyte population.

EXAMPLE 4

Since the physical principle involved in fractionation of erythrocytes in velocity sedimentation is quite different from that of equilibrium sedimentation, cells from tubes 10, 38, and 70 (from the blood bank sample represented by line 20 in FIG. 2) were subjected to buoyant density centrifugation in a stepwise gradient. The standard procedure developed by Leif and Vinograd, Proc. Nat. Acad. Sci., 51:520–524 (1964), was employed except that dextran (average molecular weight of 80,700, Sigma Chemical Company, St. Louis, Missouri) was used to adjust the density and that 4 steps of densities, 1.07, 1.08, 1.09, and 1.11 g/ml, were established in the centrifuge tubes. Erythrocytes suspended in isotonic saline were applied directly to the tops of the tubes.

Cells in tube 10 gave 2 bands, one between 1.07 and 1.08 g/ml and the other between 1.09 and 1.11 g/ml. If density is indeed linearly related to age, this result seems to suggest that cells of two different ages have a tendency to stick to each other to form clumps of about 8 cells.

Cells in tube 38 gave 3 bands, one less than 1.07 g/ml, one between 1.08 and 1.09 g/ml, and the third between 1.09 and 1.11 g/ml. Tube 38 thus contained the youngest erythrocytes as suggested by the band of lowest density. Probably three different age groups were involved in forming these cell clusters.

Finally, cells in tube 70 gave only one band between 1.08 and 1.09 g/ml. As previously indicated, the cells in tube 70 were echinocytes and were presumably on their way to lysis. However, such cells were not the oldest of the sample since their density was not the highest. Therefore, while the velocity sedimentation procedure of this invention may be used effectively to separate such cells from normal discocytes, standard equilibrium sedimentation procedures appear unable to achieve the same separation since such echinocytes do not have a unique density.

While in the foregoing we have disclosed an embodiment of the invention in considerable detail for purposes of illustration, it will be understood by those skilled in the art that many of these details may be varied without departing from the spirit and scope of the invention.

We claim:

1. A method of treating a population of red blood cells to remove those cells approaching lysis while maintaining the transfusability of the remaining cells, comprising the steps of exposing the entire red cell population to velocity sedimentation in a solution of isotonic saline buffered to a pH of about 7.4 and containing a soluble non-toxic carbolydrate cell-compatible density-adjusting agent in an amount sufficient to adjust the solution to a density within the range of about 1.005 to 1.015, collecting and separating the cells so exposed into at least two fractions based on differences in sedimentation rate, one of said fractions containing the slower sedimenting cells of said population, and retaining for transfusion that fraction that does not include said slower sedimenting cells.

2. The method of claim 1 in which said densityadjusting agent is a disaccharide or a polysaccharide.

3. The method of claim 2 in which said disaccharide or polysaccharide is selected from the group consisting of sucrose and dextran.

4. The method of claim 3 in which said disaccharide is sucrose.

5. The method of claim 1 in which said velocity sedimentation is preformed under the influence of gravity.

6. The method of claim 5 in which there is the further step of washing the retained cells in isotonic saline to substantially remove said density-adjusting agent therefrom.

7. The method of claim 6 in wich there is the further step of transfusing the washed red cells of the retained fraction.

8. A method of treating a population of red blood cells comprising both discocytes and echinocytes to remove the echinocytes without destroying the transfusability of the discocytes, comprising the steps of exposing the entire red cell population to velocity sedimentation in a solution of isotonic saline buffered to a pH of about 7.4 and containing in solution a cell-compatible disaccharide or polysaccharide in an amount sufficient to adjust the solution to a density within the range of about 1.005 to 1.015, collecting and separating the cells so exposed into at least two fractions based on differences in sedimentation rate, the red cells of one of said fractions consisting substantially entirely of echinocytes and the cells of another of said fractions consisting substantially entirely of discocytes.

9. The method of claim 8 in which there is the further step of washing the cells of a fraction consisting substantially entirely of discocytes in isotonic saline to remove disaccharide or polysaccharide from said fraction.

10. The method of claim 9 in which there is the further step of transfusing said washed discocytes.

11. The method of claims 8, 9, or 10 in which said disaccharide or polysaccharide is selected from the group consisting of sucrose and dextran.

12. The method of claims 8, 9, or 10 in which said disaccharide is sucrose.

* * * * *